(12) United States Patent
Ohnishi et al.

(10) Patent No.: US 6,863,437 B2
(45) Date of Patent: Mar. 8, 2005

(54) TEMPERATURE-RESPONSIVE POLYMER/POLYMER COMPLEX

(75) Inventors: Noriyuki Ohnishi, Yokohama (JP);
Hirotaka Furukawa, Yokohama (JP);
Kazunori Kataoka, Tokyo (JP);
Katsuhiko Ueno, Tsukuba (JP)

(73) Assignees: National Institute of Advanced Industrial Science and Technology, Tokyo (JP); Chisso Corporation, Osaka (JP)

( * ) Notice: Subject to any disclaimer, the term of this patent is extended or adjusted under 35 U.S.C. 154(b) by 0 days.

(21) Appl. No.: 10/362,167

(22) PCT Filed: Aug. 20, 2001

(86) PCT No.: PCT/JP01/07122

§ 371 (c)(1),
(2), (4) Date: Feb. 21, 2003

(87) PCT Pub. No.: WO02/16496

PCT Pub. Date: Feb. 28, 2002

(65) Prior Publication Data

US 2003/0156618 A1 Aug. 21, 2003

(30) Foreign Application Priority Data

Aug. 23, 2000 (JP) ........................................ 2000-252526

(51) Int. Cl.[7] ........................ G01N 25/20; G01K 11/16; G01K 1/00
(52) U.S. Cl. ........................ 374/43; 374/101; 374/159; 116/216; 430/964
(58) Field of Search ................................ 374/100, 101, 374/43, 159; 436/1; 430/587, 964; 428/402.24; 116/216, 206–207

(56) References Cited

U.S. PATENT DOCUMENTS

| | | | | |
|---|---|---|---|---|
| 4,743,398 A | * | 5/1988 | Brown et al. | 252/408.1 |
| 5,002,587 A | * | 3/1991 | Berendt | 8/543 |
| 5,248,555 A | * | 9/1993 | Matsushita et al. | 428/402.24 |
| 5,254,473 A | * | 10/1993 | Patel | 436/1 |
| 5,399,616 A | * | 3/1995 | Kuhn et al. | 524/765 |
| 5,443,908 A | * | 8/1995 | Matsushita et al. | 428/402.24 |
| 5,919,404 A | * | 7/1999 | Fujita et al. | 252/583 |
| 5,964,181 A | * | 10/1999 | Pereyra et al. | 116/216 |
| 6,077,908 A | * | 6/2000 | Yahiro | 525/218 |
| 6,485,978 B1 | * | 11/2002 | Kirckof et al. | 436/1 |
| 6,494,950 B1 | * | 12/2002 | Fujita et al. | 106/499 |
| 6,534,234 B1 | * | 3/2003 | Naruse et al. | 430/162 |
| 6,605,714 B2 | * | 8/2003 | Vaidya et al. | 536/55.2 |

FOREIGN PATENT DOCUMENTS

| | | | | |
|---|---|---|---|---|
| JP | 5-133947 | | 5/1993 | |
| JP | 6-116169 | | 4/1994 | |
| JP | 9-227329 | | 9/1997 | |
| JP | 2000086729 A | * | 3/2000 | ......... C08F/220/58 |
| JP | 2000-219698 | | 8/2000 | |
| WO | 99/12975 | | 3/1999 | |

OTHER PUBLICATIONS

Novel Thermo–Responsive magnetic Nanoparticles. Furukawa et al. European Cells and Materials, vol.3, Suppl. 2, 2002 (p. 78).*
Characterization of the USCI Behavior of Poly(N–acetylacrylamide) in Sugar solutions. Kato et al. Analytical Sciences 2001, vol. 17, Suppl.*
Norihiro Kato et al., "Characterization of the UCST Behavior of Poly(N–acetylacrylamide) in Sugar Solutions", Analytical Sciences, vol. 17 Supplement, pp. i1129–i1132, 2001.

* cited by examiner

Primary Examiner—Gail Verbitsky
(74) Attorney, Agent, or Firm—Wenderoth, Lind & Ponack, L.L.P.

(57) ABSTRACT

The problem of the invention is to find a polymer mixture which forms an inter-polymer complex by being responsive to temperature even under neutral to alkaline conditions. According to the invention, a temperature responsive inter-polymer complex capable of showing thermal responsiveness in an aqueous solution, which contains a poly-N-acetylacrylamide or polyvinyl alcohol and polyethylene glycol, polyacrylamide or polymethacylamide, is applied to separating agents, immobilized enzymes, denatured protein modifiers, separation method or concentration of microorganisms, purification or concentration of nucleic acids, drug-releasing microcapsules and the like.

12 Claims, No Drawings

TEMPERATURE-RESPONSIVE POLYMER/POLYMER COMPLEX

TECHNICAL FIELD

This invention relates to a temperature responsive inter-polymer complex which can be applied to separating agents, immobilized enzymes, denatured protein modifiers, separation method or concentration of microorganisms, purification or concentration of nucleic acids, drug-releasing microcapsules and the like.

BACKGROUND ART

Polyethylene oxide (PEO), polyacrylamide (PAAm), polyacrylic acid (PAAc) or polymethacrylic acid (PMAAc), which is a water-soluble polymer, dissolves in water in an aqueous solution within an optional temperature range. However, it has been described by Yoshihito Nagata and Tasuku Saito in *Nippon Kagaku Kaishi* (Journal of Japanese Chemical Society), 1, 171 (1976) that a mixed aqueous solution of PEO with PAAc or PMAAc forms an inter-polymer complex under an acidic condition, and the complex shows lower critical solution temperature (LCST) in the aqueous solution.

On the other hand, it has been described by D. J. Eustance et al. in *J. Appl. Polym. Sci.*, 35, 707 (1988) that a mixed aqueous solution of PAAm with PAAc forms an inter-polymer complex under an acidic condition, and the complex shows upper critical solution temperature (UCST).

However, the polymers shown in the above form inter-polymer complexes with polyacrylic acid (PAAc) or polymethacrylic acid (PMAAc), which are polyelectrolytes, but the inter-polymer complexes are not formed under neutral to alkaline conditions due to dissociation of carboxyl groups of the polyelectrolytes, so that the application range has a limitation.

Accordingly, an object of the invention is to find a technique by which inter-polymer complexes can be formed by being responsive to temperature even under neutral to alkaline conditions.

DISCLOSURE OF THE INVENTION

This time, we have made an attempt to form an inter-polymer complex between nonionic polymers and found as a result that an inter-polymer complex can be formed between nonionic water-soluble polymers, thus resulting in the accomplishment of the invention. That is, the invention is comprised of the following constructions.

(1) A temperature responsive inter-polymer complex capable of showing thermal responsiveness in an aqueous solution, which contains a poly-N-acetylacrylamide and polyethylene glycol.

(2) A temperature responsive inter-polymer complex capable of showing thermal responsiveness in an aqueous solution, which contains a poly-N-acetylacrylamide and polyacrylamide or polymethacrylamide.

(3) A temperature responsive inter-polymer complex capable of showing thermal responsiveness in an aqueous solution, which contains polyvinyl alcohol and polyethylene glycol.

(4) A temperature responsive inter-polymer complex capable of showing thermal responsiveness in an aqueous solution, which contains polyvinyl alcohol and polyacrylamide or polymethacrylamide.

(5) The temperature responsive inter-polymer complex described in the aforementioned (1) or (2), wherein the poly-N-acetylacrylamide is a copolymer of N-acetylacrylamide with a hydrophilic or hydrophobic monomer.

Since the aforementioned inter-polymer complex of the invention can show temperature response even under neutral to alkaline conditions, its application range is sharply extended so that, e.g., by fixing a ligand having the ability to recognize molecules, it can be broadly applied to separating agents, assay reagents, immobilized enzymes, denatured protein modifiers, separation method or concentration of microorganisms, purification or concentration of nucleic acids, drug-releasing microcapsules and the like. Thus, the invention is further comprised of the following constructions.

(6) The temperature responsive inter-polymer complex described in any one of the aforementioned (1) to (5), wherein a ligand having the ability to recognize molecules is fixed to at least one of the poly-N-acetylacrylamide, polyvinyl alcohol, polyethylene glycol, polyacrylamide and polymethacrylamide.

(7) A separating agent which uses the temperature responsive inter-polymer complex described in the aforementioned (6).

BEST MODE FOR CARRYING OUT THE INVENTION

More illustratively, a mixture of the poly-N-acetylacrylamide and polyethylene glycol, or a mixture of a copolymer of N-acetylacrylamide with a hydrophilic or hydrophobic monomer and polyacrylamide or polymethacrylamide, according to the invention, shows upper critical solution temperature (UCST) in an aqueous solution. That is, it forms an inter-polymer complex at a temperature of equal to or lower than the UCST. Particularly, it has a coacervation ability.

Also, a mixture of the poly-N-acetylacrylamide and polyacrylamide or polymethacrylamide shows lower critical solution temperature (LCST) in an aqueous solution. That is, it forms an inter-polymer complex at a temperature of equal to or higher than the LCST.

In addition, a mixture of polyvinyl alcohol and polyacrylamide or polymethacrylamide, or a mixture of polyvinyl alcohol and polyethylene glycol, shows both of UCST and LCST in an aqueous solution. That is, it forms an inter-polymer complex at a temperature of equal to or lower than UCST and of equal to or higher than LCST and has a coacervation ability.

As the aforementioned hydrophilic monomer to be copolymerized with N-acetylacrylamide, acrylamide, methacrylamide, N-methylacrylamide, N-ethylacrylamide, N,N-dimethylacrylamide, allyl alcohol and the like can be exemplified. Also, as the hydrophobic monomer to be copolymerized with N-acetylacrylamide, an acrylic acid ester, a methacrylic acid ester, styrene, an N-alkyl (preferably an alkyl having 3 or more carbon atoms) acrylamide, vinyl chloride, ethylene, propylene and the like can be exemplified.

It is desirable that the aforementioned hydrophilic or hydrophobic monomer is used at a copolymerization ratio of from 0.5 to 80%, particularly at a copolymerization ratio of from 5 to 70%, based on N-acetylacrylamide.

According to the invention, the LCST (lower critical solution temperature) means a temperature condition under which a mixture keeps a dissolved state at a specified temperature or less but aggregates by becoming insoluble in its solution at the specified temperature or more, and the UCST (upper critical solution temperature) means a temperature condition under which a mixture keeps a dissolved state at a specified temperature or more but aggregates by becoming insoluble in its solution at the specified temperature or less. That is, e.g., the term "a polymer mixture shows lower critical solution temperature (LCST) in an aqueous solution" means that it is uniformly dispersed in a solution at a specified temperature (LCST) or less but aggregates by forming an inter-polymer complex when the solution temperature is increased to the specified temperature (LCST) or more.

Molecular weight of the inter-polymer complex obtained by the invention is not particularly limited and can be optionally set in response to its use and the like. Generally, a range of from several hundred to several million is appropriate. Also, molecular weight of each polymer constituting the inter-polymer complex is not particularly limited too, but it is desirable that difference in the molecular weight between respective polymers constituting the inter-polymer complex is small. When difference in the molecular weight is small, a temperature responsive inter-polymer complex having good thermal responsiveness with less transition temperature widths of UCST and LCST is formed.

In addition, concentration of each polymer dissolved in an aqueous solution can also be optionally set in response to its use. A good temperature response can be obtained preferably at 0.1% or more. Also, in the case of an inter-polymer complex showing UCST for example, higher concentration of polymers in the aqueous solution causes a tendency of shifting the UCST to high temperature side.

Since the temperature responsive polymer mixture of the invention shows UCST or LCST even under neutral to alkaline conditions, various applications are possible. Particularly, since a ligand having the ability to recognize molecules can be fixed to any one of the polymers constituting the aforementioned temperature responsive polymer mixture, it can be broadly applied thereby to separating agents, assay reagents, immobilized enzymes, denatured protein modifiers, separation method or concentration of microorganisms, purification or concentration of nucleic acids, drug-releasing microcapsules and the like.

As the ligand having the ability to recognize molecules, antigens, antibodies, biotin and the like can be exemplified.

EXAMPLES

The invention is described further in detail in the following with reference to examples, but the invention is not restricted by these examples. In this connection, regarding the measurement of UCST and LCST in aqueous solutions, they were measured using transmittance of a visible light (550 nm). Also, the UCST or LCST was defined as a temperature for 50% transmittance of the visible light.

Example 1
(Inter-polymer Complex 1 of Poly-N-acetylacrylamide and PEG)

When 800 mg of poly-N-acetylacrylamide having a molecular weight of about 13,000 was mixed with 400 mg of polyethylene glycol having a molecular weight of about 8,500 in 10 g of purified water, an inter-polymer complex was formed showing cloudiness. When this inter-polymer complex was observed under an optical microscope, coacervates each having a diameter of about 1 micron were formed.

The thus obtained coacervates showed UCST in the aqueous solution, and the temperature was 51° C. both at the time of temperature up and temperature down. In this connection, measurement of UCST was carried out after adjusting pH of the aqueous solution to 7.4.

Example 2
(Inter-polymer Complex 2 of Poly-N-acetylacrylamide and PEG)

When 800 mg of poly-N-acetylacrylamide having a molecular weight of about 13,000 was mixed with 800 mg of polyethylene glycol having a molecular weight of about 8,500 in 10 g of purified water, an inter-polymer complex in the form of coacervates was formed.

The thus obtained coacervates showed UCST in the aqueous solution, and the temperature was 76° C. at the time of temperature up and 80° C. at the time of temperature down. In this connection, measurement of UCST was carried out after adjusting pH of the aqueous solution to 7.4.

Example 3
(Inter-polymer Complex 3 of Poly-N-acetylacrylamide and PEG)

When 1.4 g of poly-N-acetylacrylamide having a molecular weight of about 13,000 was mixed with 320 mg of polyethylene glycol having a molecular weight of about 3,000 in 10 g of purified water, an inter-polymer complex in the form of coacervates was formed.

The thus obtained coacervates showed UCST in the aqueous solution, and the temperature was 23° C. at the time of temperature up and 10° C. at the time of temperature down. In this connection, measurement of UCST was carried out after adjusting pH of the aqueous solution to 7.4.

Example 4
(Inter-polymer Complex of Poly-N-acetylacrylamide and Polyacrylamide)

When 1.3 g of poly-N-acetylacrylamide having a molecular weight of about 13,000 was mixed with 1.4 g of polyacrylamide having a molecular weight of about 14,000 in 10 g of purified water, an inter-polymer complex was formed.

The thus obtained inter-polymer complex showed LCST in the aqueous solution, and the temperature was 23° C. both at the time of temperature up and temperature down. In this connection, measurement of LCST was carried out after adjusting pH of the aqueous solution to 7.4.

Example 5
(Inter-polymer Complex 1 of N-acetylacrylamide-acrylamide (1:2) Copolymer and Polyacrylamide)

When 200 mg of an N-acetylacrylamide-acrylamide (1:2) copolymer having a molecular weight of about 340,000 was mixed with 8 mg of polyacrylamide having a molecular weight of about 10,000 in 10 g of purified water, an inter-polymer complex in the form of coacervates was formed.

The thus obtained coacervates showed UCST in the aqueous solution, and the temperature was 35° C. both at the time of temperature up and temperature down. In this connection, measurement of UCST was carried out after adjusting pH of the aqueous solution to 7.4.

Example 6
(Inter-polymer Complex 2 of N-acetylacrylamide-acrylamide (1:2) Copolymer and Polyacrylamide)

When 400 mg of an N-acetylacrylamide-acrylamide (1:2) copolymer having a molecular weight of about 340,000 was mixed with 16 mg of polyacrylamide having a molecular weight of about 10,000 in 10 g of purified water, an inter-polymer complex in the form of coacervates was formed.

The thus obtained coacervates showed UCST in the aqueous solution, and the temperature was 66° C. both at the time of temperature up and temperature down. In this connection, measurement of UCST was carried out after adjusting pH of the aqueous solution to 7.4.

Example 7
(Inter-polymer Complex 3 of N-acetylacrylamide-acrylamide (1:2) Copolymer and Polyacrylamide)

When 400 mg of an N-acetylacrylamide-acrylamide (1:2) copolymer having a molecular weight of about 340,000 was mixed with 16 mg of polyacrylamide having a molecular weight of about 10,000 in 10 g of PBS saline buffer solution, an inter-polymer complex in the form of coacervates was formed.

The thus obtained coacervates showed UCST in the aqueous solution, and the temperature was 34° C. both at the time of temperature up and temperature down. In this connection, measurement of UCST was carried out after adjusting pH of the aqueous solution to 7.4.

Example 8
(Inter-polymer Complex of Polyvinyl Alcohol and Polyethylene Glycol)

When 1 g of polyvinyl alcohol having a molecular weight of about 16,000 was mixed with 500 mg of polyethylene glycol having a molecular weight of about 8,000 in 10 g of purified water, an inter-polymer complex in the form of coacervates was formed.

The thus obtained coacervates showed UCST in the aqueous solution, and the temperature was 42° C. both at the time of temperature up and temperature down. In this connection, measurement of UCST was carried out after adjusting pH of the aqueous solution to 7.4.

Example 9
(Inter-polymer Complex of Polyvinyl Alcohol (80% Hydrolysate) and Polyacrylamide)

When 400 mg of polyvinyl alcohol (80% hydrolysate) having a molecular weight of about 10,000 was mixed with 400 mg of polyacrylamide having a molecular weight of about 10,000 in 10 g of PBS saline buffer solution, an inter-polymer complex in the form of coacervates was formed.

The thus obtained coacervates showed LCST and UCST in the aqueous solution. The LCST was 35° C. both at the time of temperature up and temperature down, and the UCST was 84° C. both at the time of temperature up and temperature down. In this connection, measurement of LCST was carried out after adjusting pH of the aqueous solution to 7.4.

While the invention has been described in detail and with reference to specific embodiments thereof, it will be apparent to one skilled in the art that various changes and modifications can be made therein without departing from the spirit and scope thereof.

This application is based on Japanese Patent Application No. 2000-252526 applied on Aug. 23, 2000, the entire contents thereof being hereby incorporated by reference.

INDUSTRIAL APPLICABILITY

The polymer mixture of the invention forms a polymer complex by being responsive to temperature and shows UCST and/or LCST in an aqueous solution even under neutral to alkaline conditions.

Thus, by fixing a ligand having the ability to recognize molecules to anyone of components of the polymer mixture, it can be broadly applied to various separating agents, assay reagents, denatured protein modifiers, agents for purifying nucleic acids, drug-releasing microcapsules and the like.

What is claimed is:

1. A temperature responsive inter-polymer complex capable of showing thermal responsiveness in an aqueous solution, which comprises a poly-N-acetylacrylamide and polyethylene glycol, wherein a ligand having the ability to recognize molecules is fixed to at least one of the poly-N-acetylacrylamide and polyethylene glycol.

2. A separating agent which uses the temperature responsive inter-polymer complex according to claim 1.

3. A temperature responsive inter-polymer complex capable of showing thermal responsiveness in an aqueous solution, which comprises a poly-N-acetylacrylamide and polyacrylamide or polymethacrylamide, wherein the poly-N-acetylacrylamide is a copolymer of N-acetylacrylamide with a hydrophilic or hydrophobic monomer.

4. A separating agent which uses the temperature responsive inter-polymer complex according to claim 3.

5. A temperature responsive inter-polymer complex capable of showing thermal responsiveness in an aqueous solution, which comprises a poly-N-acetylacrylamide and polyacrylamide or polymethacrylamide, wherein a ligand having the ability to recognize molecules is fixed to at least one of the poly-N-acetylacrylamide, polyacrylamide and polymethacrylamide.

6. A separating agent which uses the temperature responsive inter-polymer complex according to claim 5.

7. A temperature responsive inter-polymer complex capable of showing thermal responsiveness in an aqueous solution, which comprises polyvinyl alcohol and polyethylene glycol, wherein a ligand having the ability to recognize molecules is fixed to at least one of the polyvinyl alcohol and polyethylene glycol.

8. A separating agent which uses the temperature responsive inter-polymer complex according to claim 7.

9. A temperature responsive inter-polymer complex capable of showing thermal responsiveness in an aqueous solution, which comprises polyvinyl alcohol and polyacrylamide or polymethacrylamide, wherein a ligand having the ability to recognize molecules is fixed to at least one of the polyvinyl alcohol, polyacrylamide and polymethacrylamide.

10. A separating agent which uses the temperature responsive inter-polymer complex according to claim 9.

11. A temperature responsive inter-polymer complex capable of showing thermal responsiveness in an aqueous solution, which comprises a poly-N-acetylacrylamide and polyethylene glycol, wherein the poly-N-acetylacrylamide is a copolymer of N-acetylacrylamide with a hydrophilic or hydrophobic monomer, and wherein a ligand having the ability to recognize molecules is fixed to at least one of the poly-N-acetylacrylamide and polyethylene glycol.

12. A separating agent which uses the temperature responsive inter-polymer complex according to claim 11.

* * * * *